United States Patent [19]
Berthiaume

[11] Patent Number: 5,591,194
[45] Date of Patent: Jan. 7, 1997

[54] TELESCOPING BALLOON CATHETER AND METHOD OF USE

[75] Inventor: William A. Berthiaume, Billerica, Mass.

[73] Assignee: C. R. Bard, Inc., Murray Hill, N.J.

[21] Appl. No.: 485,655

[22] Filed: Jun. 7, 1995

Related U.S. Application Data

[63] Continuation of Ser. No. 198,628, Feb. 18, 1994, abandoned.

[51] Int. Cl.$^6$ .................................................. A61M 29/00
[52] U.S. Cl. .............................. 606/192; 606/194; 604/96
[58] Field of Search ................................. 606/191, 193, 606/194, 195, 197, 198, 192; 604/96, 99, 97, 101, 103, 102

[56] References Cited

U.S. PATENT DOCUMENTS

| | | | |
|---|---|---|---|
| 4,449,532 | 5/1984 | Storz | 128/341 |
| 4,564,014 | 1/1986 | Fogarty et al. | 606/194 |
| 4,862,891 | 9/1989 | Smith | 606/191 |
| 5,171,222 | 12/1992 | Euteneuer et al. | 606/194 X |
| 5,217,482 | 6/1993 | Keith | 606/194 |
| 5,300,085 | 4/1994 | Yock | 606/194 X |
| 5,342,297 | 8/1994 | Jang | 606/194 |
| 5,387,226 | 2/1995 | Miraki | 606/194 |

Primary Examiner—Michael Powell Buiz
Assistant Examiner—Kevin Truong
Attorney, Agent, or Firm—Morgan & Finnegan, L.L.P.

[57] ABSTRACT

A catheter wherein the "effective over-the-wire" length is adjustable. The catheter includes an elongated inflation shaft having a longitudinal inflation lumen, an extension shaft disposed distal to the inflation shaft and through which the inflation lumen is continued, a balloon element disposed at the distal end of the extension shaft and in fluid communication with the inflation lumen, a guidewire shaft having a longitudinal guidewire lumen which extends from the distal end of the balloon member, through the balloon member and the extension shaft, to the proximal end of the extension shaft, and a telescoping portion. The telescoping portion comprising first and second telescoping tubes which are slidably mounted on the inflation shaft and the extension shaft. The first and second telescoping tubes are sized so that the first telescoping tube can be retracted into the second telescoping tube. The extension shaft is sized so that it can be retracted into the first telescoping tube. The effective "over-the-wire length" of the telescoping balloon catheter can be reduced by retracting the first telescoping tube and the extension tube into the second telescoping tube. In another embodiment, the telescoping portion comprises three telescoping tubes, which results in a greater reduction of the effective "over-the-wire length."

27 Claims, 4 Drawing Sheets

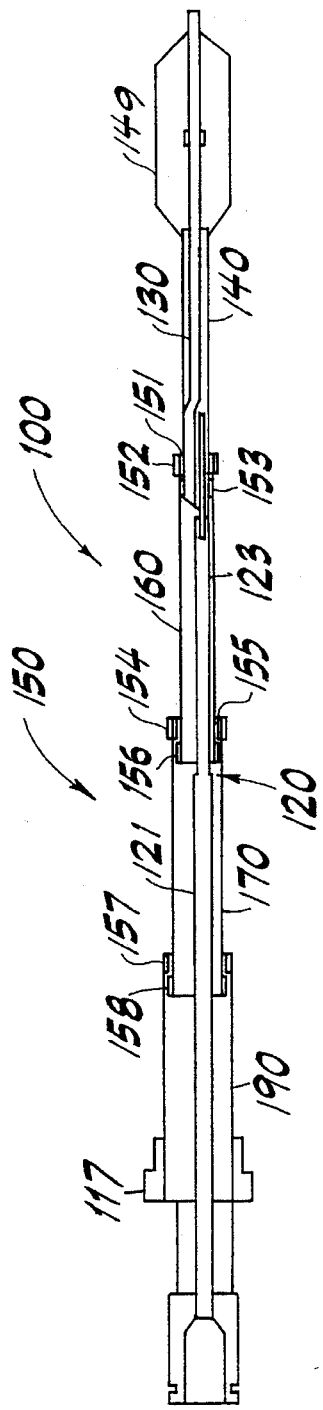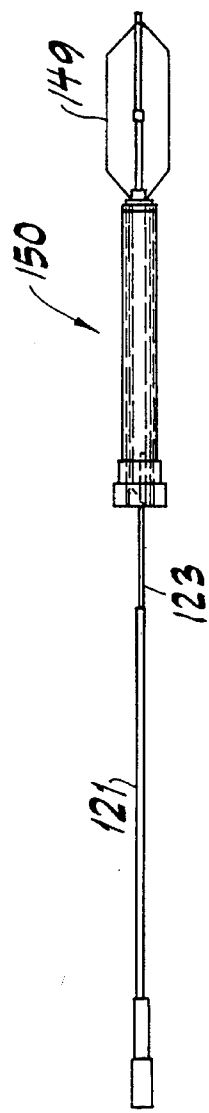
FIG. 8
FIG. 9

TELESCOPING BALLOON CATHETER AND METHOD OF USE

This is a continuation of application Ser. No. 08/198,628, filed on Feb. 18, 1994, now abandoned.

FIELD OF THE INVENTION

This invention relates to catheters placed in the body of a patient such as in the cardiovascular system and, in particular, to a catheter which permits exchange of the catheter while maintaining in the patient the guidewire over which the catheter is inserted.

BACKGROUND OF THE INVENTION

Catheters are placed at various locations within a patient for a wide variety of purposes and medical procedures. For example only, one type of catheter is a balloon dilatation catheter which is used in the treatment of a vascular stenosis. Such a catheter has a balloon at its distal end which is intended to be placed, in a deflated condition, within the stenosis, and then inflated while in the stenosis to expand radially the stenosed lumen of the blood vessel. Typically, the placement of such catheters involves the use of a guidewire which may be advanced through the patient's vasculature to the location which is to be treated. The catheter, which has a guidewire lumen adapted to receive the guidewire, then is advanced over the wire to the stenosis, or, alternatively, the wire and catheter may be advanced in unison to the stenosis with the wire protruding from the distal end of the catheter.

Essentially, there are three types of catheters: "over-the-wire" catheters, "monorail" catheters and "fixed balloon on a wire" catheters.

An over-the-wire catheter comprises a guidewire lumen which extends the entire length of the catheter. The guidewire is disposed entirely within the catheter except for the distal and proximal portions of the guidewire which extend beyond the distal and proximal ends of the catheter respectively. A typical over-the-wire balloon dilatation catheter is disclosed in Simpson et al. U.S. Pat. No. 4,323,071.

Over-the-wire catheters have many advantages traceable to the presence of a full-length guidewire lumen such as good stiffness and pushability for readily advancing the catheter through the tortuous vasculature to the stenosis, and the availability of the guidewire lumen for transporting radiocontrast dye to the stenosis or for pressure measurements.

However, over-the-wire catheters do suffer some shortcomings. For example, it often becomes necessary, in the performance of a catheter procedure, to exchange the indwelling catheter for another catheter having a different size balloon. In order to maintain a guidewire in position while withdrawing the catheter, the guidewire must be gripped at its proximal end to prevent it from being pulled out of the blood vessel with the catheter. However, the catheter, which may typically be on the order of 135 centimeters long, is longer than the proximal portion of the standard guidewire which protrudes out of patient. For this reason, in order to effectuate an exchange of an over-the-wire catheter, a wire of the order of 300 centimeters long is necessary.

In one type of over-the-wire catheter exchange, the guidewire first is removed from the lumen of the indwelling catheter. Then a longer exchange wire is passed through the catheter to replace the original wire. Then, while holding the exchange wire by its proximal end to maintain it in place, the catheter is withdrawn proximally from the blood vessel over the exchange wire. After the first catheter has been removed, the next catheter is then threaded onto the proximal end of the exchange wire and is advanced along the exchange wire and through the patient's blood vessels until the distal end of the catheter is located as desired. The exchange wire may be permitted to remain in place or may be exchanged for a shorter, conventional length guidewire. Alternatively, the length of the initial guidewire may be extended by way of a guidewire extension apparatus (see Gambale et al. U.S. Pat. No. 4,917,103).

However, with either exchange process, the long length of the exchange wire dictates that two operators are needed to perform the procedure. During the procedure, it is necessary that the operators communicate with each other which makes the procedure time consuming. Furthermore, the long length of the exchange wire renders it awkward to handle.

These shortcomings of the over-the-wire catheters led to the development of the monorail type catheter. Catheters of this type, which are described in U.S. Pat. Nos. B1 4,762,129, 5,040,548 and 5,061,273, are formed so that the guidewire is located outside of the catheter except for a short segment at the distal end of the catheter, which passes over the wire. The distal segment of the catheter has a short lumen which extends from the distal tip of the catheter to a more proximally located opening near the distal tip. In use, the guidewire is placed initially in the patient's vascular system. The distal segment of the catheter then is threaded onto the wire. The catheter can be advanced alongside the wire with its distal segment being attached to and guided along the wire. The catheter can be removed and exchanged for another catheter without the use of the usual double length exchange wire and without requiring withdrawal of the initially placed guidewire.

Although such a monorail catheter system may avoid the requirement for using a long exchange wire, it presents several difficulties. For example, it is not possible to exchange guidewires in an indwelling catheter as can be done with over-the-wire catheters. Additionally, the device presents a potential for damaging the delicate inner surface of an artery from a tension load applied to the guidewire which would tend to straighten the artery. Also, there is an increased risk of guidewire entanglement in those procedures where multiple guidewires are used, because the guidewires are exposed within the blood vessel.

The monorail catheters, which do not include a guidewire lumen for the entire length of the catheter, also lack the desired stiffness and pushability for readily advancing the catheter through tortuous blood vessels. In addition, the lack of a full length guide-wire lumen deprives the physician of an additional lumen that may be used for other purposes, e.g., pressure measurement and distal dye injection.

There is, therefore, a need for a new and improved catheter apparatus which incorporates the benefits of both the over-the-wire and the monorail catheters but without their attendant drawbacks.

In general, it is an object of the present invention to provide a catheter apparatus which facilitates both the rapid exchanges of the indwelling catheter without the use of an extension wire while providing sufficient stiffness and pushability to readily advance the catheter apparatus through the tortuous vasculature.

SUMMARY OF THE INVENTION

In accordance with the invention, a telescoping balloon catheter is provided for insertion into a patient over an elongated guidewire. The catheter includes an elongated inflation shaft having a longitudinal inflation lumen, an extension shaft disposed distal to the inflation shaft and through which the inflation lumen is continued, a balloon member disposed at the distal end of the extension shaft and in fluid communication with the inflation lumen, a guidewire shaft having a longitudinal guidewire lumen which extends from the distal end of the balloon member, through the balloon member and the extension shaft, to the proximal end of the extension shaft, and a telescoping portion. The telescoping portion comprises first and second telescoping tubes which are slidably mounted on the inflation shaft and the extension shaft. The first and second telescoping tubes are sized so that the first telescoping tube can be retracted into the second telescoping tube. Further, the extension shaft is sized so that it can be retracted into the first telescoping tube.

During the advancement of the telescoping balloon catheter, the telescoping portion is fully extended so that the telescoping balloon catheter is an over-the-wire catheter for the full extent of its length. When the telescoping balloon catheter is being exchanged for another catheter, the effective "over-the-wire length" of the telescoping balloon catheter can be significantly reduced by retracting the first telescoping tube and the extension tube into the second telescoping tube. Since the effective "over-the-wire length" of the telescoping balloon catheter can be reduced to a length less than the proximal portion of a standard guidewire protruding from the patient's body, an exchange of the indwelling catheter can be effected without the use of an extension wire.

BRIEF DESCRIPTION OF THE DRAWINGS

The invention will be further described, by way of example, with reference to the accompanying drawings, wherein:

FIG. 8 is a cross-sectional view of another embodiment of the balloon catheter of the invention wherein the telescoping portion comprises three telescoping tubes.

FIG. 9 is a side view of the telescoping balloon catheter of the invention wherein the three-tube telescoping portion is in the fully retracted position.

DETAILED DESCRIPTION OF THE PREFERRED EMBODIMENTS

Figure 1:
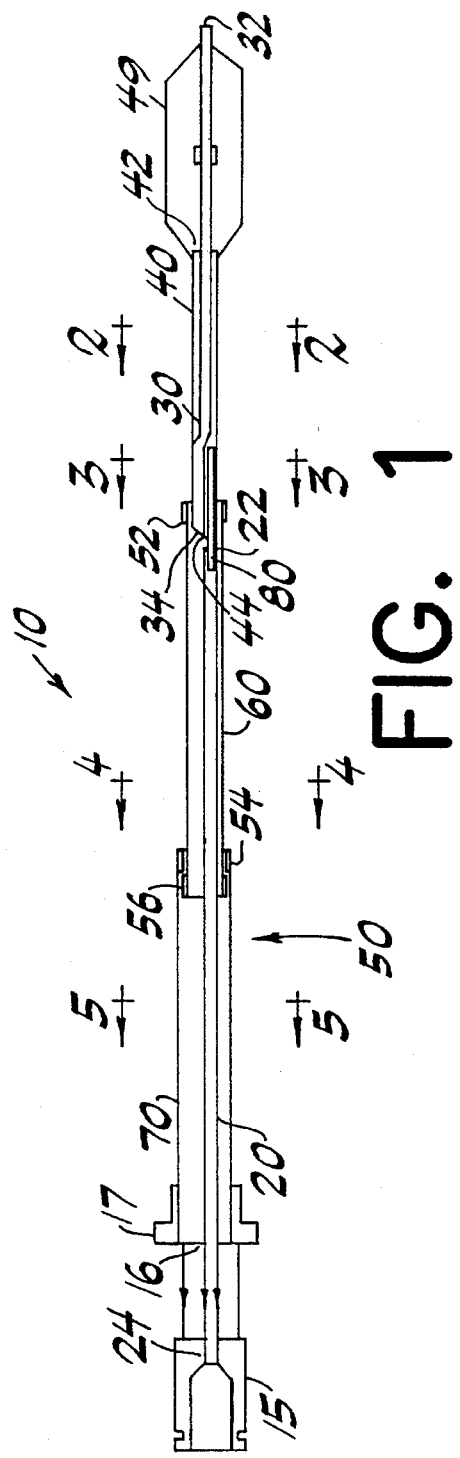
FIG. 1 is a cross-sectional view of the telescoping balloon catheter of the invention with the telescoping portion in the fully-extended position.

It should be noted that while the following description will be specifically in the context of coronary angioplasty dilatation catheters, the invention is not so limited and is applicable to other catheter assemblies.

Referring to FIGS. 1–5, the telescoping balloon catheter of the invention, which is designated generally as 10, includes an elongated inflation shaft 20, a guidewire shaft 30, an extension shaft 40, a balloon member 49, and telescoping portion 50.

The elongated inflation shaft 20 has an open distal end 22 and an open proximal end 24, and an inflation lumen 26 extending therethrough. The inflation shaft 20 is to be formed from stainless steel hypotube in order to lend stiffness and pushability to the catheter 10.

The inflation shaft 20 does not extend for the entire length of catheter 10. The extension shaft 40, which is substantially shorter than the inflation shaft, has an open distal end 42 and open proximal end 44 and an extension lumen 46 extending therethrough. The extension shaft 40 is disposed distal to the inflation shaft 20 and the extension lumen 46 is in fluid communication with and extends the inflation lumen 26 through the extent of the extension shaft 40. The extension shaft 40 is to be formed from a flexible polymer such as polyvinyl chloride, polyethylene terephthalate or, preferably, high density polyethylene. In preferred embodiment, the inflation shaft 20 is not directly affixed to the extension shaft 40; rather an extension tube 80 is disposed between the inflation shaft 20 and the extension shaft 40, and provides the fluid communication pathway between the inflation lumen 26 and the extension lumen 46. In a more preferred embodiment, the extension tube 80 is formed from stainless steel hypotube.

The balloon member 49 is disposed at the distal end of extension shaft 40. The balloon member 49 may be formed from polyvinyl chloride, polyethylene, polyurethane or preferably, polyethylene terephthalate. The interior of the balloon member 49 is in fluid communication with inflation lumen 26 by way of the extension lumen 46. A fitting 15 is secured to the proximal end of elongated inflation shaft 20 in a suitable manner. Preferably, the fitting 15 is in the form of a female luer fitting. The balloon member 49 is inflated by injecting inflation fluid through the fitting 15, and subsequently deflated by withdrawing the inflation fluid through the fitting 15. Preferably, a spacer element 13 is disposed on inflation shaft 20 distal of the fitting 15.

The guidewire shaft 30 has an open distal end 32 and an open proximal end 34, and a guidewire lumen 36 extending therethrough. The guidewire shaft 30 is to be formed from a flexible polymer such as polyvinyl chloride, polyethylene terephthalate or, preferably, high density polyethylene. The guidewire shaft 30 is disposed within the extension shaft 40 and extends through balloon member 49. The proximal end 34 of the guidewire shaft 30 is co-extensive with the proximal end 44 of the extension shaft 40. The distal end of balloon member 49 is affixed to guidewire shaft 30. The distal end of the guidewire shaft 30 extends beyond the distal end of the balloon member 49.

Figure 2:
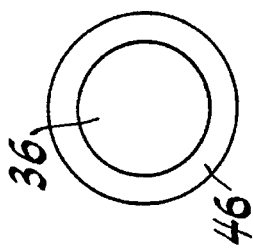
FIG. 2 is a cross-sectional view of the telescoping balloon catheter when viewed along the line 2—2 in FIG. 1.
Figure 3:
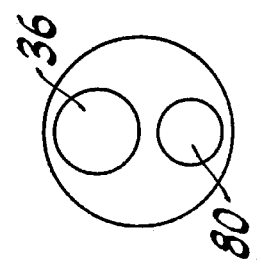
FIG. 3 is a cross-sectional view of the telescoping balloon catheter when viewed along line 3—3 in FIG. 1.
Figure 4:
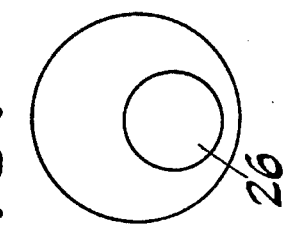
FIG. 4 is a cross-sectional view of the telescoping balloon catheter when viewed along lines 4—4 in FIG. 1.
Figure 5:
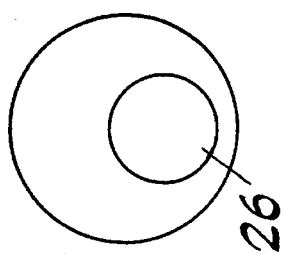
FIG. 5 is a cross-sectional view of the telescoping balloon catheter when viewed along lines 5—5 in FIG. 1.

The guidewire lumen 36 is sized such that a standard coronary angioplasty guidewire (not shown) can be slidably received within guidewire lumen 36. As shown in FIG. 2, the outer diameter of the guidewire shaft 30 is such that the extension lumen 46 is maintained within the extension shaft 40 in the form of an annular flow passage with sufficient inflation fluid flow capability to ensure acceptable balloon inflation and deflation rates. As shown in FIG. 3, at the proximal portion of the extension shaft 40, the proximal portion of the guidewire shaft 30 and the distal portion of extension tube 80 are disposed in a "side-by-side" arrangement or a dual lumen arrangement.

The telescoping portion 50 comprises a first telescoping tube 60 and a second telescoping tube 70 which are both slidably mounted on the inflation shaft 20 and the extension shaft 40. The first and second telescoping tubes 60 and 70 are to be formed from a flexible polymer such as polyvinyl chloride, polyethylene, polyethylene terephthalate or, preferably, polyimide. The inner diameter of the second telescoping tube 70 is greater than the outer diameter of the first telescoping tube 60 so that the first telescoping tube 60 can be slidably received within the second telescoping tube 70. The first and second telescoping tubes 60 and 70 are relatively thin in thickness so as not to present too much of a discontinuity on the catheter exterior surface.

A series of stop members are employed to limit the positioning of the first and second telescoping tubes along the inflation shaft 20 and the extension shaft 40.

A stop member 52 is disposed on the outer surface of first telescoping tube 60 at the distal end thereof. The stop member 52 is sized so that the distal end of the second telescoping tube 70 cannot be maneuvered distal of, or beyond, the distal end of the first telescoping member 60. Preferably, the stop member 52 comprises a piece of tubing of minimal length, an inner diameter about equivalent to the outer diameter of the first telescoping tube 60, and an outer diameter greater than the inner diameter of the second telescoping tube 70. More preferably, stop member 52 is formed from the same material as the first telescoping tube 60.

A stop member 54 is disposed on the inner surface of the second telescoping tube 70 at the distal end thereof. A stop member 56 is disposed on the outer surface of the first telescoping tube 60 at the proximal end thereof. The stop members 54 and 56 are sized so as to engage and prevent the proximal end of the first telescoping tube 60 from being maneuvered distal of, or beyond, the distal end of the second telescoping tube 70. In a preferred embodiment, stop member 54 comprises a piece of tubing of minimal length and an outer diameter about equivalent to the inner diameter of the second telescoping tube 70. The stop member 56 comprises a piece of tubing of minimal length and an inner diameter about equivalent to the outer diameter of the first telescoping tube 60. The outer diameter of the stop member 56 is greater than the inner diameter of the stop member 54. More preferably, the stop members 56 and 54 are formed from the same materials as first and second telescoping tubes 60 and 70, respectively.

The outer diameter of the deflated balloon member 49 is greater than the inner diameter of the first telescoping tube 60 so that first telescoping tube 60 cannot be maneuvered beyond the balloon member 49.

An anti-backbleed hub 17 is affixed to the proximal end of second telescoping tube 70. The anti-backbleed hub 17 limits the leakage of blood through the catheter 10. The anti-backbleed hub 17 also acts to restrict the maneuverability of telescoping tubes 60 and 70. The anti-backbleed hub 17 has a central port 16 through which the inflation shaft 20 and the guidewire can be passed.

Coronary angioplasty dilatation catheters are, typically, 135 centimeters long. The length of the first telescoping tube 60 and the second telescoping tube 70 are preferably about equal. The combined length of telescoping tubes 60 and 70 when in the fully extended position (i.e., proximal end of first telescoping tube 60 is located at the distal end of second telescoping tube 70) is substantially less than the combined length of the inflation shaft 20 and extension shaft 40. As an example only, for a catheter of 135 cm in length, the length of both the first and second telescoping tubes is 44 cm and the length of the extension shaft 40 is 47 cm. As depicted in FIG. 1, when the telescoping portion 50 is in the fully extended position, the distal end of first telescoping tube 60 is distal of the proximal end of extension shaft 40. Thus, when the telescoping portion 50 is in the fully extended position, the guidewire would be encased by the guidewire shaft 30 and the telescoping tubes 60 and 70, and not outside of the catheter at any point along the extent of the catheter 10. The catheter 10, therefore, is an over-the-wire catheter for the full extent of its length when the telescoping portion 50 is in the fully extended position.

Operation and use of the telescoping balloon catheter 10 shown in FIG. 1 may now be briefly described as follows. A guiding catheter (not shown in FIGS.) is inserted into the coronary artery in a conventional manner. Preparatory to insertion into a patient, the telescoping portion 50 is maneuvered into the fully extended position. The guidewire is then introduced into telescoping balloon catheter 10 by a back loading technique. The proximal extremity of the guidewire is inserted backwardly through the distal end of catheter 10 through open distal end 32 of guidewire shaft 30. The guidewire is advanced rearwardly by holding the distal portion of catheter 10 in one hand and, with the other hand, advancing the guidewire rearwardly through guidewire lumen 36, first telescoping tube 60, and second telescoping tube 70 until its proximal portion protrudes from the anti-backbleed hub 17. The proximal portion of the guidewire is pulled rearwardly until the distal end of the guidewire is at about the distal end of catheter 10. In this arrangement, catheter 10 is an over-the-wire catheter for the full extent of its length.

Catheter 10 and the guidewire are advanced into the guiding catheter in a conventional manner. Next, the guidewire is maneuvered through the tortuous coronary arteries to the site of the stenosis. Catheter 10 is advanced along the guidewire until balloon member 49 is located across the stenosis.

The first telescoping tube 60 is sized such that there is sufficient frictional contact between the inner surface and the outer surface of the extension shaft 40 so that, during the advancing of the catheter 10 to the stenosis, the distal end of the first telescoping tube 60 will not be forced proximally to a position proximal of the proximal end of the extension shaft 40. This frictional contact ensures that catheter 10 remains an over-the-wire catheter for the full extent of its length when the balloon member 49 is located across the stenosis. Since the telescoping portion 50 is in the fully extended position, medications such as heparin, saline or radiocontrast dye, can be delivered to the stenosis site by way of injection through the telescoping tubes 60 and 70 and the guidewire lumen 36. This passageway may also be utilized to obtain pressure measurements at the stenosis site.

The advancement of the catheter 10 along the guidewire is facilitated by the increased stiffness and pushability of the catheter 10 to which is attributable to the fully extended telescoping portion 50.

As soon as it has been established that the balloon member 49 has been positioned across the stenosis, inflation pressure can be applied through fitting 15 by the use of a hand syringe or another pressurizing device well known in the art (not shown in FIGS.). The inflation of the balloon member 49 can be observed if radiographic contrast liquid is used as the inflation fluid. Inflating the balloon member 49 dilates the stenosis by stretching the coronary artery and simultaneously pressing the stenosis into the artery wall.

Occasionally, the stenosis does not dilate to an acceptable extent. In this instance, the cardiologist will elect to exchange the indwelling catheter for another catheter with a different sized balloon. When replacing a typical over-the-wire catheter, it is necessary that the guidewire protrude from the patient's body by a length greater than the length of the dilatation catheter. With respect to catheter 10 of this invention, a standard length guidewire is sufficient to effectuate a catheter exchange because the effective "over-the-wire length" of catheter 10 can be reduced by way of the telescoping portion 50.

Figure 6:
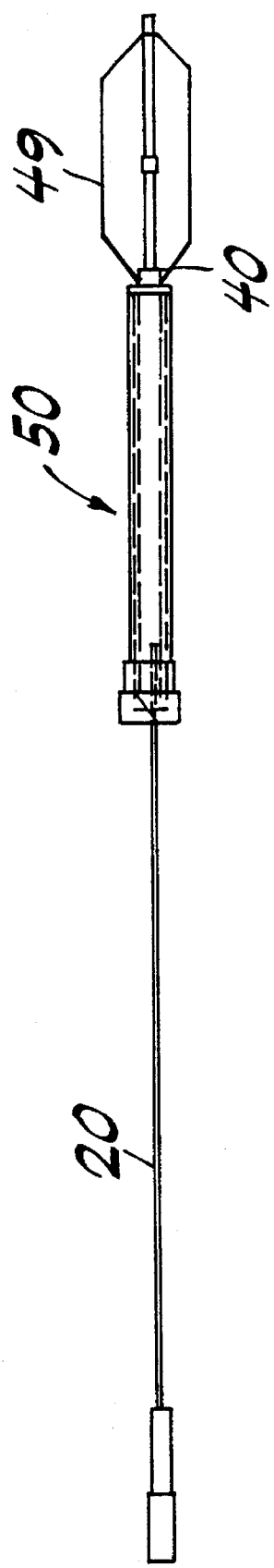
FIG. 6 is a side view of the telescoping balloon catheter of the invention with the first telescoping tube and the extension tube retracted into the second telescoping tube.

During catheter exchange procedures, it is desirable to maintain the guidewire in position across the stenosis. To effect an exchange of catheter 10, the guidewire is gripped by the cardiologist with one hand just proximal of the anti-backbleed hub 17. With the other hand, the cardiologist grips the fitting 15 and pulls the inflation shaft 20 proximally from the anti-backbleed hub 17. As a result of the frictional contact between the inner surface of the first telescoping tube 60 and the outer surface of the extension shaft 40, the continued proximally-directed withdrawal of the inflation shaft 20 causes the first telescoping tube 60 to be retracted into the second telescoping tube 70 until the stop member 52 engages the distal end of the second telescoping tube 70 by stop member 54 and/or the proximal end of the first telescoping tube 60 engages the anti-backbleed hub 17. The continued proximally-directed withdrawal of the inflation shaft 20 next causes the extension shaft 40 to be retracted into the first telescoping tube 60, which remains located within the second telescoping tube 70, until the deflated balloon member 49 engages the distal end of the first telescoping tube 60 (see FIG. 6). In this manner, the effective "over-the-wire length" of catheter 10 will be reduced to the combined length of the second telescoping tube 70 and the balloon member 49. As an example only, for a catheter of an overall length of 135 cm and where the length of both the first and second telescoping tubes is 44 cm and the length of the extension shaft 40 is 47 cm, the effective "over-the-wire length" may be reduced to 47 cm.

Next, the catheter 10 is backed-off the guidewire in a conventional manner. The effective "over-the-wire" length is sized to be less than the length of a standard guidewire that protrudes from the patient's body so that an extension wire will not be needed to effect an exchange of catheter 10.

Figure 7:
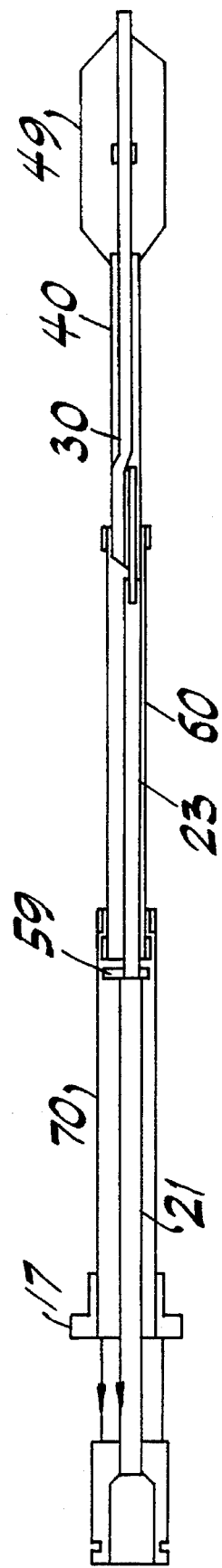
FIG. 7 is a cross-sectional view of another embodiment of the balloon catheter of the invention with the telescoping portion in the fully-extended position.

Referring to FIG. 7, in a more preferred embodiment, the elongated inflation shaft 20 has a distal portion 23 and a proximal portion 21. The inner diameter of the proximal portion 21 is greater than the inner diameter of the distal portion 23. The larger inner diameter of proximal portion 21 results in reduced deflation times for the balloon member 49. A stop member 59 is disposed at the proximal end of the distal portion 23 of the inflation shaft 20. The stop member 59 is sized so as to prevent the first telescoping tube 60 from migrating proximally during the advancing of the catheter to the stenosis.

FIG. 8 illustrates another embodiment of the subject catheter which is designated generally as 100. In this embodiment, the telescoping portion comprises three telescoping tubes rather than two tubes. The minimum effective "over-the-wire length" achievable with a telescoping portion comprised of three telescoping tubes is significantly less than that achievable with a telescoping portion comprised of two telescoping tubes.

The telescoping balloon catheter 100 includes an elongated inflation shaft 120 comprised of a distal portion 123 and a proximal portion 121 with an inner diameter greater than that of the distal portion 123, a guidewire shaft 130, an extension shaft 140, a balloon member 149 and a telescoping portion 150. Since the structure of catheter 100 generally corresponds to the structure of the above-described catheter 10 except for the telescoping portion 150, the following description will be limited to the structure and operation of the telescoping portion 150.

The telescoping portion 150 comprises a first telescoping tube 160, a second telescoping tube 170 and a third telescoping tube 190, all of which are slidably mounted on the inflation shaft 120 and the extension shaft 140. The telescoping tubes are to be formed from a flexible polymer such as polyvinyl chloride, polyethylene, polyethylene terephthalate or, preferably, polyimide. The inner diameter of the third telescoping tube 190 is greater than the outer diameter of the second telescoping tube 170. Similarly, the inner diameter of the second telescoping tube 170 is greater than the outer diameter of the first telescoping tube 160. Thus, the first telescoping tube 160 can be slidably received within the second telescoping tube 170, and both the first and second telescoping tubes 160 and 170, can be slidably received within the third telescoping tube 190. The telescoping tubes are relatively thin in thickness so as not to present too much of a discontinuity on the catheter exterior surface.

A series of stop members are employed to limit the positioning of the first, second and third telescoping tubes along the inflation shaft 120 and the extension shaft 140.

A stop member 151 is disposed on the inner surface of the first telescoping tube 160 at the distal end thereof. A stop member 153 is disposed on the outer surface of the extension shaft 140 at the proximal end thereof. The stop members 151 and 153 are sized so as to engage and prevent the proximal end of the extension shaft 140 from being maneuvered distal of the distal end of the first telescoping tube 160.

A stop member 152 is disposed on the outer surface of the first telescoping tube 160 at the distal end thereof. A stop member 155 is disposed on the inner surface of the second telescoping tube 170 at the distal end thereof. The stop members 152 and 155 are sized so as to engage and prevent the distal end of the second telescoping tube 170 from being maneuvered distal of the distal end of first telescoping tube 160.

A stop member 156 is disposed on the outer surface of the first telescoping tube 160 at the proximal end thereof. The stop members 156 and 155 are sized so as to engage and prevent the proximal end of the first telescoping tube 160 from being maneuvered distal of the distal end of the second telescoping tube 170.

A stop member 154 is disposed on the outer surface of the second telescoping tube 170 at the distal end thereof. A stop member 157 is disposed on the inner surface of the third telescoping tube 190 at the distal end thereof. The stop members 154 and 157 are sized so as to engage and prevent the distal end of the third telescoping tube 190 from being maneuvered distal of the distal end of the second telescoping tube 170.

A stop member 158 is disposed on the outer surface of the second telescoping tube 170 at the proximal end thereof. Stop members 158 and 157 are sized so as to engage and prevent the proximal end of the second telescoping tube 170 from being maneuvered distal of the distal end of the third telescoping tube 190.

The outer diameter of the deflated balloon member 149 is greater than the inner diameter of the first telescoping tube 160 so that the first telescoping tube 160 cannot be maneuvered beyond the balloon member 149.

An anti-backbleed hub 117 is affixed to the proximal end of the third telescoping tube 190. The anti-backbleed hub 117 acts to restrict the maneuverability of the telescoping tubes.

When the telescoping portion 150 is in the fully extended position, the guidewire would be encased by the guidewire shaft 130 and the telescoping tubes 160, 170, and 190, and not outside of the catheter at any point along the extent of the catheter 100. The length of the first telescoping tube 160, the second telescoping tube 170, and the third telescoping tube 190 are, preferably, about equal. By example only, for a catheter with an overall length of 135 cm, the length of each telescoping tube may be 33 cm and the length of the extension shaft 140 may be 35 cm. For a catheter of these dimensions, the effective "over-the-wire length" may be reduced to 35 cm.

The effective "over-the-wire length" of catheter 100 may be reduced in a manner essentially the same as that described above for catheter 10. The inflation shaft 120 is withdrawn proximally from the anti-backbleed hub 117. As a result of the frictional contact between the inner surface of the first telescoping tube 160 and the outer surface of the extension shaft 140, the continued proximally-directed withdrawal of the inflation shaft 120 causes the first telescoping tube 160 to be retracted into the second telescoping tube 170 until the stop member 152 engages the distal end of second telescoping tube 170 by stop member 155. The continued proximally-directed withdrawal of the inflation shaft 120 next causes the second telescoping tube 170 and the indwelling first telescoping tube 160 to be retracted into the third telescoping tube 190 until the stop member 154 engages the distal end of the third telescoping tube 190 by stop member 157 and/or the proximal end of the second telescoping tube 170 engages the anti-backbleed hub 117. The continued proximally-directed withdrawal of the inflation shaft 120 next causes the extension shaft 140 to be retracted into the first telescoping tube 160, which remains located within the second and third telescoping tubes, until the deflated balloon member engages the distal end of the first telescoping tube 160. (See FIG. 9).

The adjustable structure of the catheter allows for an alternative method of use. As previously explained, a guiding catheter (not shown in FIGS.) is inserted into the coronary artery in a conventional manner. Rather than first back-loading the guidewire into the catheter, the guidewire alone is inserted into the guiding catheter and then advanced to the site of the stenosis. Preparatory to loading the catheter onto the indwelling guidewire, the telescoping portion 50 or 150 is maneuvered into the fully retracted position so that the effective "over-the-wire length" of the catheter is at a minimum (see FIGS. 6 and 9). The distal portion of the catheter is then loaded onto the proximal portion of the indwelling guidewire in a conventional manner. The catheter is then advanced over the indwelling catheter to the site of the stenosis. The catheter may be removed from the patient's vasculature by continually withdrawing the inflation shaft until the proximal portion of the fully retracted telescoping portion protrudes from the guiding catheter and then the catheter is backed off in a conventional manner.

Having described the invention in specific detail and exemplified the manner in which it may be carried into practice, it will now be readily apparent to those skilled in the art that innumerable variations, applications, modifications and extensions of the basic principles involved may be made without departing from its sphere or scope.

What is claimed is:

1. A balloon dilatation catheter with a variable effective over-the-wire length, i.e. a variable guidewire lumen length, that is adapted to be utilized with a conventional length guidewire without resort to an exchange guidewire or a guidewire extension apparatus, comprising:

an elongated inflation shaft having open proximal and distal ends and a longitudinal inflation lumen extending therethrough;

an extension shaft disposed distal to said inflation shaft, said extension shaft having open proximal and distal ends and a lumen extending therethrough that is in fluid communication with and extends said inflation lumen through the extent of said extension shaft and, said proximal end of said extension shaft connected to said distal end of said inflation shaft;

a guidewire shaft having open proximal and distal ends and a guidewire lumen extending therethrough, said guidewire shaft being coextensive with said extension shaft over the length of said extension shaft, said proximal end of said guidewire shaft being adjacent to said proximal end of said extension shaft, said guidewire shaft distal end extending distal of said extension shaft distal end, and said guidewire lumen sized to slidably receive said conventional length guidewire;

an inflatable balloon having a distal end and a proximal end, said proximal end of said balloon sealingly affixed to said distal end of said extension shaft, said distal end of said balloon sealingly affixed to said guidewire shaft at about said guidewire shaft distal end, and the interior of said balloon in fluid communication with said inflation lumen; and telescoping means slidably mounted on said inflation shaft and said extension shaft for adjustably extending the length of said guidewire lumen.

2. The balloon dilatation catheter defined in claim 1 wherein said telescoping means comprises a first telescoping tube having distal and proximal ends, and a second telescoping tube having distal and proximal ends, said second telescoping tube having an inner diameter sized to permit said first telescoping tube to be retracted into said second telescoping tube, and said first telescoping tube having an inner diameter sized to permit said extension shaft to be retracted into said first telescoping tube but smaller than said balloon when deflated thereby preventing the retration of said balloon into said first telescoping tube, the length of said guidewire lumen is determined by the extent that said first telescoping tube is retracted into said second telescoping tube such that when said distal end of said second telescoping tube is positioned at said proximal end of said first telescoping tube and said distal end of said first telescoping tube is positioned at said proximal end of said extension shaft the length of said guidewire lumen is at a maximum value and when said extension shaft and first telescoping tube are fully retracted into said second telescoping tube the length of said guidewire lumen is at a minimum value.

3. The balloon dilatation catheter defined in claim 2 which further comprises an anti-backbleed hub disposed at said proximal end of said second telescoping tube, said anti-backbleed hub has a central port so that said inflation shaft and said guidewire can be extended through said anti-backbleed hub.

4. The balloon dilatation catheter defined in claim 3 which further comprises a first stopping means associated with said first telescoping tube for preventing the maneuvering of said distal end of said second telescoping tube distal to said distal end of said first telescoping tube.

5. The balloon dilatation catheter defined in claim 4 which further comprises a second stopping means associated with said first and second telescoping tubes for preventing the maneuvering of said proximal end of said first telescoping tube distal to said distal end of said second telescoping tube.

6. The balloon dilatation catheter defined in claim 5 wherein said inflation shaft is formed from hypotube.

7. The balloon dilatation catheter defined in claim 1 wherein said telescoping means comprises a first telescoping tube having distal and proximal ends, a second telescoping tube having proximal and distal ends, and a third telescoping tube having proximal and distal ends, said third tube having an inner diameter sized to permit said second telescoping tube to be retracted into said third telescoping tube, said second telescoping tube having an inner diameter sized to permit said first telescoping tube to be retracted into said second telescoping tube, and said first telescoping tube having an inner diameter sized to permit said extension shaft to be retracted into said first telescoping tube but smaller than said balloon when deflated thereby preventing the retraction of said balloon into said first telescoping tube, the extent of the retraction of said first telescoping tube into said second telescoping tube and of said second telescoping tube into said third telescoping tube determines the length of said guidewire lumen such that when said distal end of said third telescoping tube is positioned at said proximal end of said second telescoping tube, said distal end of said second telescoping tube is positioned at said proximal end of said first telescoping tube and said distal end of said first telescoping tube is positioned at said proximal end of said extension shaft the length of said guidewire lumen is at a maximum value and when said extension shaft, first telescoping tube and second telescoping tube are fully retracted into said third telescoping tube the length of said guidewire lumen is at a minimum value.

8. The balloon dilatation catheter defined in claim 7 which further comprises an anti-backbleed hub disposed at said proximal end of said third telescoping tube, said anti-backbleed hub having a central port so that said inflation shaft and said guidewire can be extended through said anti-backbleed hub.

9. The balloon dilatation catheter defined in claim 8 wherein said inflation shaft is formed from hypotube.

10. A balloon dilatation catheter with a variable effective over-the-wire length, i.e. a variable guidewire lumen length, that is adapted to be utilized with a conventional length guidewire without resort to an exchange wire or a guidewire extension apparatus, comprising:

an elongated inflation shaft having open proximal and distal ends and a longitudinal inflation lumen extending therethrough;

an extension shaft disposed distal to said inflation shaft, said extension shaft having open proximal and distal ends and a lumen extending therethrough that is in fluid communication with and extends said inflation lumen through the extent of said extension shaft, and said proximal end of said extension shaft connected to said distal end of said inflation shaft;

a guidewire shaft having open proximal and distal ends and a guidewire lumen extending therethrough, said guidewire shaft being coextensive with said extension shaft over the length of said extension shaft, said proximal end of said guidewire shaft being adjacent to said proximal end of said extension shaft, said guidewire shaft distal end extending distal of said extension shaft distal end, and said guidewire lumen sized to slidably receive said conventional length guidewire;

an inflatable balloon having a distal end and a proximal end, said proximal end of said balloon sealingly affixed to said distal end of said extension shaft, said distal end of said balloon sealingly affixed to said guidewire shaft at about said guidewire shaft distal end and the interior of said balloon in fluid communication with said inflation lumen;

a first telescoping tube having distal and proximal ends, said first telescoping tube slidably mounted on said inflation shaft and said extension shaft so as to be extendable over at least a portion of a guidewire extending proximally from said guidewire lumen extending through said guidewire shaft so as to extend the length of said guidewire lumen, said first telescoping tube having an inner diameter sized to permit said extension shaft to be retracted into said first telescoping tube as said inflation shaft is withdrawn from a patient's body but smaller than said balloon when deflated so that said balloon cannot be retracted into said first telescoping tube; and a second telescoping tube having distal and proximal ends, said first telescoping tube slidably mounted on said inflation shaft and said extension shaft so as to be extendable over at least a portion of a guidewire extending proximally from said guidewire lumen extending through said guidewire shaft and said first telescoping tube so as to extend the length of said guidewire lumen, said second telescoping tube having an inner diameter sized to permit said first telescoping tube and said extension shaft to be retracted into second telescoping tube as said inflation shaft continues to be withdrawn from a patient's body, and said second telescoping tube operatively associated with said first telescoping tube so that the length of said guidewire lumen will be reduced as a result of the withdrawal of said inflation shaft from a patient's body.

11. The balloon dilatation catheter defined in claim 10 which further comprises an anti-backbleed hub disposed at said proximal end of said second telescoping tube, said anti-backbleed hub has a central port so that said inflation shaft and said guidewire can be extended through said anti-backbleed hub.

12. The balloon dilatation catheter defined in claim 11 which further comprises a first stopping means associated with said first telescoping tube for preventing the maneuvering of said distal end of said second telescoping tube distal to said distal end of said first telescoping tube.

13. The balloon dilatation catheter defined in claim 12 which further comprises a second stopping means associated with said first and second telescoping tubes for preventing the maneuvering of said proximal end of said first telescoping tube distal to said distal end of said second telescoping tube.

14. The balloon dilatation catheter defined in claim 13 wherein said inflation shaft is formed from hypotube.

15. A balloon dilatation catheter with a variable effective over-the-wire length, i.e. a variable guidewire lumen length, that is adapted to be utilized with a conventional length guidewire without resort to an exchange guidewire or a guidewire extension apparatus, comprising:

an elongated inflation shaft formed from hypotube having open proximal and distal ends and a longitudinal inflation lumen extending therethrough;

an extension tube having open proximal and distal ends and a lumen extending therethrough, said extension tube proximal end connected to said distal end of said inflation shaft, and said lumen is in fluid communication with and extends said inflation lumen through the extent of said extension tube, an extension shaft having open proximal and distal ends and an extension lumen extending therethrough, said proximal end of said extension shaft connected to said distal end of said extension tube, and said extension lumen is in fluid communication with and extends said inflation lumen through the extent of said extension shaft, a guidewire shaft having open proximal and distal ends and a guidewire lumen extending therethrough, said guidewire shaft being coextensive with said extension shaft over the length of said extension shaft, said proximal end of said guidewire shaft being adjacent to said proximal end of said extension shaft, said guidewire shaft distal end extending distal of said extension shaft distal end, and said guidewire lumen sized to slidably receive said conventional length guidewire;

an inflatable balloon having a distal end and a proximal end, said proximal end of said balloon sealingly affixed to said distal end of said extension shaft, said distal end of said balloon sealingly affixed to said guidewire shaft about said guidewire shaft distal end and the interior of said balloon in fluid communication with said inflation lumen;

a first telescoping tube having distal and proximal ends, said first telescoping tube slidably mounted on said inflation shaft, extension tube and extension shaft so as to be extendable over at least a portion of a guidewire extending proximally from said guidewire lumen extending through said guidewire shaft so as to extend the length of said guidewire lumen, said first telescoping tube having an inner diameter sized to permit said extension shaft to be retracted into said first telescoping tube as said inflation shaft is withdrawn from a patient's body but smaller than said balloon when deflated so that said balloon cannot be retracted into said first telescoping tube; and a second telescoping tube having distal and proximal ends, said first telescoping tube slidably mounted on said inflation shaft, extension tube and extension shaft so as to be extendable over at least a portion of a guidewire extending proximally from said guidewire lumen extending through said guidewire shaft and said first telescoping tube so as to extend the length of said guidewire lumen, said second telescoping tube having an inner diameter sized to permit said first telescoping tube and said extension shaft to be retracted into said second telescoping tube as said inflation shaft continues to be withdrawn from a patient's body, and said second telescoping tube operatively associated with said first telescoping tube so that the length of said guidewire lumen will be reduced as a result of the withdrawal of said inflation shaft from a patient's body.

16. The balloon dilatation catheter defined in claim 15 which further comprises a first stopping means associated with said first telescoping tube for preventing the maneuvering of said distal end of said second telescoping tube distal to said distal end of said first telescoping tube.

17. The balloon dilatation catheter defined in claim 16 which further comprises a second stopping means associated with said first and second telescoping tubes for preventing the maneuvering of said proximal end of said first telescoping tube distal to said distal end of said second telescoping tube.

18. A balloon dilatation catheter with a variable effective over-the-wire, i.e. a variable guidewire lumen length, length that is adapted to be utilized with a conventional length guidewire without resort to an exchange guidewire or a guidewire extension apparatus, comprising:

an elongated inflation shaft having open proximal and distal ends and a longitudinal inflation lumen extending therethrough;

an extension shaft disposed distal to said inflation shaft, said extension shaft having open proximal and distal ends and a lumen extending therethrough that is in fluid communication with and extends said inflation lumen through the extent of said extension shaft, and said proximal end of said extension shaft connected to said distal end of said inflation shaft;

a guidewire shaft having open proximal and distal ends and a guidewire lumen extending therethrough, said guidewire shaft being coextensive with said extension shaft over the length of said extension shaft, said proximal end of said guidewire shaft being adjacent to said proximal end of said extension shaft, said guidewire shaft distal end extending distal of said extension shaft distal end, and said guidewire lumen sized to slidably receive said conventional length guidewire;

an inflatable balloon having a distal end and a proximal end, said proximal end of said balloon sealingly affixed to said distal end of said extension shaft, said distal end of said balloon sealingly affixed to said guidewire shaft at about said guidewire shaft distal end and the interior of said balloon in fluid communication with said inflation lumen;

a first telescoping tube having distal and proximal ends, said first telescoping tube slidably mounted on said inflation shaft and said extension shaft so as to be extendable over at least a portion of a guidewire extending proximally from said guidewire lumen extending through said guidewire shaft so as to extend the length of said guidewire lumen, said first telescoping tube having an inner diameter sized to permit said extension shaft to be retracted into said first telescoping tube as said inflation shaft is withdrawn from a patient's body but smaller than said balloon when deflated so that said balloon cannot be retracted into said first telescoping tube; and a second telescoping tube having distal and proximal ends, said first telescoping tube slidably mounted on said inflation shaft and said extension shaft so as to be extendable over at least a portion of a guidewire extending proximally from said guidewire lumen extending through said guidewire shaft and first telescoping tube so as to extend the length of said guidewire lumen, said second telescoping tube having an inner diameter sized to permit said first telescoping tube and said extension shaft to be retracted into said second telescoping tube as said inflation shaft continues to be withdrawn from a patient's body; and a third telescoping tube having distal and proximal ends, said third telescoping tube slidably mounted on said inflation shaft and said extension shaft so as to be extendable over at least a portion of a guidewire extending proximally from said guidewire lumen extending through said guidewire shaft, said first telescoping tube and said second telescoping tube so as to extend the length of said guidewire lumen, said third telescoping tube having an inner diameter sized to permit said second telescoping tube, said first telescoping tube and said extension shaft to be retracted into said third telescoping tube as said inflation shaft continues to be withdrawn from a patient's body, and said third telescoping tube operatively associated with said first and second telescoping tubes so that the length of said guidewire lumen will be reduced as a result of the withdrawal of said inflation shaft from a patient's body.

19. A method for advancing a balloon dilatation catheter with a variable effective over-the-wire length, i.e. a variable guidewire lumen length, to the stenosis site where the catheter is an over-the-wire catheter over the full extent of its length and rapidly exchanging said catheter without making use of an exchange guidewire or a guidewire extension apparatus by reducing the effective over-the-wire length of said catheter, said balloon dilatation catheter having an elongated inflation shaft having open proximal end distal ends and a longitudinal inflation lumen extending therethrough, an extension shaft disposed distal to said inflation shaft, said extension shaft having open proximal and distal ends and a lumen extending therethrough that is in fluid communication with and extends said inflation lumen through the extent of said extension shaft, a guidewire shaft having open proximal end, distal ends and a guidewire lumen extending therethrough, said proximal end of said guidewire shaft being adjacent to said proximal end of said extension shaft, said guidewire shaft being coextensive with said extension shaft over the length of said extension shaft said guidewire shaft distal end extending distal of said extension shaft distal end, an inflatable balloon having a distal end and a proximal end, said balloon proximal end sealingly affixed to said distal end of said extension shaft, said balloon distal end sealingly affixed to said guidewire shaft about said guidewire shaft distal end and the interior of said balloon in fluid communication with said inflation lumen, a first telescoping tube slidably mounted on said inflation shaft and said extension shaft so as to be extendable over at least a portion of a guidewire extending proximally from said guidewire lumen extending through said guidewire shaft so as to extend the length of said guidewire lumen, said first telescoping tube having an inner diameter sized to permit said extension shaft to be retracted into said first telescoping tube as said inflation shaft is withdrawn from a patient's body but smaller than said balloon when deflated so that said balloon cannot be retracted into said first telescoping tube, a second telescoping tube slidably mounted on said inflation shaft and said extension shaft so as to be extendable over at least a portion of a guidewire extending proximally from said guidewire lumen extending through said guidewire shaft and said first telescoping tube so as to extend the length of said guidewire lumen, said second telescoping tube having an inner diameter sized to permit said first telescoping tube to be retracted into second telescoping tube, and said second telescoping tube operatively associated with said first telescoping tube so that the effective over-the-wire length of said balloon dilatation catheter will be reduced as a result of a withdrawal of said inflation shaft from a patient's body, and an anti-backbleed hub disposed at said proximal end of said second telescoping tube, said anti-backbleed hub has a central port so that said inflation shaft and said guidewire can be extended through said anti-backbleed hub, said method comprising the steps of:

(a) maneuvering said first and second telescoping tubes to substantially the fully extended position such that said proximal end of said first telescoping tube is located at about said distal end of said second telescoping tube;

(b) introducing a conventional length guidewire, which has a distal end and a proximal end, into said balloon dilatation catheter through said guidewire lumen and rearwardly advancing said guidewire through said first and second telescoping tubes until said guidewire proximal end protrudes from said anti-backbleed hub;

(c) pulling said proximal end of said guidewire until said guidewire distal end is at about said distal end of said balloon dilatation catheter;

(d) inserting said balloon dilatation catheter and guidewire into a guiding catheter that has been inserted in a patient's vasculature;

(e) advancing said guidewire and said balloon dilatation catheter to a stenosis site;

(f) holding said guidewire in position at said stenosis site by gripping said guidewire at a position just proximal of said anti-backbleed hub;

(g) gripping said inflation shaft and withdrawing said inflation shaft through said anti-backbleed hub;

(h) continuing to withdraw said inflation shaft so that said first telescoping tube is fully retracted into said second telescoping tube;

(i) continuing to withdraw said inflation shaft so that said extension shaft is fully retracted into said first telescoping tube;

(j) gripping said guidewire at a position proximal of said anti-backbleed hub with a first hand;

(k) gripping said inflation shaft with a second hand and rearwardly advancing said inflation shaft to said position of said first hand gripping said guidewire;

(l) repeating steps (j)–(k) until said balloon dilatation catheter distal end is withdrawn from said patient; and (m) gripping said guidewire at a position distal of said balloon dilatation catheter distal end and pulling said balloon dilatation catheter off said proximal end of said guidewire.

20. A method for advancing a balloon dilatation catheter with a variable effective over-the-wire length, i.e. a variable guidewire lumen length, to the stenosis site where said catheter is an over-the-wire catheter over the full extent of its length and rapidly exchanging said catheter without making use of an exchange wire or a guidewire extension apparatus by reducing the effective over-the-wire length of said catheter, said balloon dilatation catheter having an elongated inflation shaft formed from hypotube having open proximal and distal ends and a longitudinal inflation lumen extending therethrough, an extension tube having open proximal and distal ends and a lumen extending therethrough, said extension tube proximal end connected to said distal end of said inflation shaft, and said lumen is in fluid communication with and extends said inflation lumen through the extent of said extension tube, an extension shaft having open proximal and distal ends and an extension lumen extending therethrough, said proximal end of said extension shaft connected to said distal end of said extension tube, and said extension lumen is in fluid communication with and extends said inflation lumen through the extent of said extension shaft, a guidewire shaft having open proximal and distal ends and a guidewire lumen extending therethrough, said proximal end of said guidewire shaft being adjacent to said proximal end of said extension shaft, said guidewire shaft being coextensive with said extension shaft over the length of said extension shaft, said guidewire shaft distal end extending distal of said extension shaft distal end, an inflatable balloon having a distal end and a proximal end, said proximal end of said balloon sealingly affixed to said distal end of said extension shaft, said distal end of said balloon sealingly affixed to said guidewire shaft about said guidewire shaft distal end and the interior of said balloon in fluid communication with said inflation lumen, a first telescoping tube having distal and proximal ends, said first telescoping tube slidably mounted on said inflation shaft, extension tube and said extension shaft so as to be extendable over at least a portion of a guidewire extending proximally from said guidewire lumen extending through said guidewire shaft so as to extend the length of said guidewire lumen, said first telescoping tube having an inner diameter sized to permit said extension shaft to be retracted into said first telescoping tube as said inflation shaft is withdrawn from a patient's body but smaller than said balloon when deflated so that said balloon cannot be retracted into said first telescoping tube, a second telescoping tube having distal and proximal ends, said second telescoping tube slidably mounted on said inflation shaft, extension tube and extension shaft so as to be extendable over at least a portion of a guidewire extending proximally from said guidewire lumen extending through said guidewire shaft and said first telescoping tube so as to extend the length of said guidewire lumen, said second telescoping tube having an inner diameter sized to permit said first telescoping tube to be retracted into second telescoping tube, said second telescoping tube operatively associated with said first telescoping tube so that the effective over-the-wire length of said balloon dilatation catheter will be reduced as a result of a withdrawal of said inflation shaft from a patient's body, and an anti-backbleed hub disposed at said proximal end of said second telescoping tube, said anti-backbleed hub has a central port so that said inflation shaft and said guidewire can be extended through said anti-backbleed hub, said method comprising the steps of:

(a) maneuvering said first and second telescoping tubes to substantially the fully extended position such that said proximal end of said first telescoping tube is located at about said distal end of said second telescoping tube;

(b) introducing a conventional length guidewire, which has a distal end and a proximal end, into said balloon dilatation catheter through said guidewire lumen and rearwardly advancing said guidewire through said first and second telescoping tubes until said guidewire proximal end protrudes from said anti-backbleed hub;

(c) pulling said proximal end of said guidewire until said guidewire distal end is at about said distal end of said balloon dilatation catheter;

(d) inserting said balloon dilatation catheter and guidewire into a guiding catheter that has been inserted in a patient's vasculature;

(e) advancing said guidewire and said balloon dilatation catheter to a stenosis site;

(f) holding said guidewire in position at said stenosis site by gripping said guidewire at a position just proximal of said anti-backbleed hub;

(g) gripping said inflation shaft and withdrawing said inflation shaft through said anti-backbleed hub;

(h) continuing to withdraw said inflation shaft so that said first telescoping tube is fully retracted into said second telescoping tube;

(i) continuing to withdraw said inflation shaft so that said extension shaft is fully retracted into said first telescoping tube;

(j) gripping said guidewire at a position proximal of said anti-backbleed hub with a first hand;

(k) gripping said inflation shaft with a second hand and rearwardly advancing said inflation shaft to said position of said first hand gripping said guidewire;

(l) repeating steps (j)–(k) until said balloon dilatation catheter distal end is withdrawn from said patient; and (m) gripping said guidewire at a position distal of said balloon dilatation catheter distal end and pulling said balloon dilatation catheter off said proximal end of said guidewire.

21. A method for advancing a balloon dilatation catheter with a variable effective over-the-wire length, i.e. a variable guidewire lumen length, to the stenosis site where the catheter is an over-the-wire catheter over the full extent of its length and rapidly exchanging said catheter without making use of an exchange guidewire or a guidewire extension apparatus by reducing the effective over-the-wire length of said catheter, said balloon dilatation catheter having an elongated inflation shaft having open proximal and distal ends and a longitudinal inflation lumen extending therethrough, an extension shaft disposed distal to said inflation shaft, said extension shaft having open proximal and distal ends and a lumen extending therethrough that is in fluid communication with and extends said inflation lumen through the extent of said extension shaft, a guidewire shaft having open proximal and distal ends and a guidewire lumen extending therethrough, said proximal end of said guidewire shaft being adjacent to said proximal end of said extension shaft, said guidewire shaft being coextensive with said extension shaft over the length of said extension shaft said guidewire shaft distal end extending distal of said extension shaft distal end, an inflatable balloon having a distal end and a proximal end, said balloon proximal end sealingly affixed to said distal end of said extension shaft, said balloon distal end sealingly affixed to said guidewire shaft about said guidewire shaft distal end and the interior of said balloon in fluid communication with said inflation lumen, a first telescoping tube slidably mounted on said inflation shaft and said extension shaft so as to be extendable over at least a portion of a guidewire extending proximally from said guidewire lumen extending through said guidewire shaft so as to extend the length of said guidewire lumen, said first telescoping tube having an inner diameter sized to permit said extension shaft to be retracted into said first telescoping tube as said inflation shaft is withdrawn from a patient's body but smaller than said balloon when deflated so that said balloon cannot be retracted into said first telescoping tube, a second telescoping tube slidably mounted on said inflation shaft and said extension shaft so as to be extendable over at least a portion of a guidewire extending proximally from said guidewire lumen extending through said guidewire shaft and said first telescoping tube so as to extend the length of said guidewire lumen, said second telescoping tube having an inner diameter sized to permit said first telescoping tube to be retracted into said second telescoping tube, a third telescoping tube slidably mounted on said inflation shaft and said extension shaft so as to be extendable over at least a portion of a guidewire extending proximally from said guidewire lumen extending through said guidewire shaft, said first telescoping and said second telescoping tube so as to extend the length of said guidewire lumen, said third telescoping tube having an inner diameter sized to permit said second telescoping tube to be retracted into said third telescoping tube, and said third telescoping tube operatively associated with said first and second telescoping tubes so that the effective over-the-wire length of said balloon dilatation catheter will be reduced as a result of a withdrawal of said inflation shaft from a patient's body, and an anti-backbleed hub disposed at said proximal end of said second telescoping tube, said anti-backbleed hub has a central port so that said inflation shaft and said guidewire can be extended through said anti-backbleed hub, said method comprising the steps of:

(a) maneuvering said first, second and third telescoping tubes to substantially the fully extended position such that said proximal end of said first telescoping tube is located at about said distal end of said second telescoping tube and the proximal end of said second telescoping tube is located at about said distal end of said third telescoping tube;

(b) introducing a conventional length guidewire, which has a distal end and a proximal end, into said balloon dilatation catheter through said guidewire lumen and rearwardly advancing said guidewire through said first, second and third telescoping tubes until said guidewire proximal end protrudes from said anti-backbleed hub;

(c) pulling said proximal end of said guidewire until said guidewire distal end is at about said distal end of said balloon dilatation catheter;

(d) inserting said balloon dilatation catheter and guidewire into a guiding catheter that has been inserted in a patient's vasculature;

(e) advancing said guidewire and said balloon dilatation catheter to a stenosis site;

(f) holding said guidewire in position at said stenosis site by gripping said guidewire at a position just proximal of said anti-backbleed hub;

(g) gripping said inflation shaft and withdrawing said inflation shaft through said anti-backbleed hub;

(h) continuing to withdraw said inflation shaft so that said first telescoping tube is fully retracted into said second telescoping tube;

(i) continuing to withdraw said inflation shaft so that said second telescoping tube is fully retracted into said third telescoping tube;

(j) continuing to withdraw said inflation shaft so that said extension shaft is fully retracted into said first telescoping tube;

(k) gripping said guidewire at a position of said anti-backbleed hub with a first hand;

(l) gripping said inflation shaft with a second hand and rearwardly advancing said inflation shaft to said position of said first hand gripping said guidewire;

(m) repeating steps (k)–(l) until said balloon dilatation catheter distal end is withdrawn from said patient; and (n) gripping said guidewire at a position distal of said balloon dilatation catheter distal end and pulling said balloon dilatation catheter off said proximal end of said guidewire.

22. A telescoping catheter comprising:

a first elongated catheter member having a proximal end and a distal end; and a second tubular catheter member having a proximal end and a distal end and an inner diameter sized so that said first elongated catheter member is slidably received within said second tubular catheter member, said second tubular catheter member comprising a first telescoping tube having distal and proximal ends, and a second telescoping tube having distal and proximal ends, said second telescoping tube having an inner diameter sized to permit said first telescoping tube to be retracted into said second telescoping tube, and said first elongated catheter member extending from said distal end of said first telescoping tube to beyond said proximal end of said second telescoping tube, said distal end of said first elongated catheter member engageable with said distal end of said first telescoping tube so that withdrawal of said first elongated catheter member through said proximal end of said second tubular catheter member will cause said first telescoping tube to be retracted into said second telescoping tube.

23. A telescoping catheter comprising:

a first elongated catheter member having a proximal end and a distal end; and a second catheter member having a proximal end and a distal end and an inner diameter sized so that said first elongated catheter member is slidably received within said second tubular catheter member, said second tubular catheter member comprising a first telescoping tube having distal and proximal ends, a second telescoping tube having distal and proximal ends and a third telescoping tube having distal and proximal ends, said second telescoping tube having an inner diameter sized to permit said first telescoping tube to be retracted into said second telescoping tube, said third telescoping tube having an inner diameter sized to permit said second telescoping tube to be retracted into said third telescoping tube, and said first elongated catheter member extending from said distal end of said first telescoping tube to beyond said proximal end of said third telescoping tube, said distal end of said first elongated catheter member engageable with said distal end of said first telescoping tube and said first telescoping tube engageable with said second telescoping tube so that withdrawal of said first elongated catheter member through the proximal end of said second tubular catheter member will cause said first telescoping tube to be retracted into said second telescoping tube and said second telescoping tube to be retracted into said third telescoping tube.

24. A method for using a telescoping catheter, said telescoping catheter having a first elongated catheter member having a proximal end and a distal end, and a second tubular catheter member having a proximal end and a distal end and an inner diameter sized so that said first catheter member is slidably received within said second tubular catheter member, said second tubular catheter member comprising a first telescoping tube having distal and proximal ends, and a second telescoping tube having distal and proximal ends, said second telescoping tube having an inner diameter sized to permit said first telescoping tube to be retracted into said second telescoping tube, and said first elongated catheter member extending from said distal end of said first telescoping tube to beyond said proximal end of said second telescoping tube, said distal end of said first elongated catheter member engageable with said distal end of said first telescoping tube so that withdrawal of said first elongated catheter member through said proximal end of said second tubular catheter member will cause said first telescoping tube to be retracted into said second telescoping tube, said method comprising the steps of:

(a) maneuvering said first and second telescoping tubes to a substantially fully extended position such that said proximal end of said first telescoping tube is located at about said distal end of said second telescoping tube;

(b) inserting said telescoping catheter into a patient's vasculature;

(c) advancing said catheter to a predetermined location within said patient's vasculature;

(d) gripping said proximal end of said first catheter member and withdrawing said first catheter member through said second tubular catheter member;

(e) continuing to withdraw said first catheter member so that said first telescoping tube is fully retracted into said second telescoping tube; and (f) gripping said proximal end of said second tubular catheter member and removing said telescoping catheter from said patient's vasculature.

25. A method for using a telescoping catheter, said telescoping catheter having a first elongated catheter member having a proximal end and a distal end, and a second tubular catheter member having a proximal end and a distal end and an inner diameter sized so that said first catheter member is slidably received within said second tubular catheter member, said second tubular catheter member comprising a first telescoping tube having distal and proximal ends, a second telescoping tube having distal and proximal ends and a third telescoping tube having distal and proximal ends, said second telescoping tube having an inner diameter sized to permit said first telescoping tube to be retracted into said second telescoping tube, said third telescoping tube having an inner diameter sized to permit said second telescoping tube to be retracted into said third telescoping tube, and said first elongated catheter member extending from said distal end of said first telescoping tube to beyond said proximal end of said third telescoping tube, said distal end of said first elongated catheter member engageable with said distal end of said first telescoping tube and said first telescoping tube engageable with said second telescoping tube so that withdrawal of said first elongated catheter member through the proximal end of said second tubular catheter member will cause said first telescoping tube to be retracted into said second telescoping tube and said second telescoping tube to be retracted into said third telescoping tube, said method comprising the steps of:

(a) maneuvering said first, second and third telescoping tubes to a substantially fully extended position such that said proximal end of said first telescoping tube is located at about said distal end of said second telescoping tube and the proximal end of said second telescoping tube is located at about the distal end of said third telescoping tube;

(b) inserting said telescoping catheter into a patient's vasculature;

(c) advancing said telescoping catheter to a predetermined location within said patient's vasculature;

(d) gripping the proximal end of said first catheter member and withdrawing said first catheter member through said second tubular catheter member;

(e) continuing to withdraw said first catheter member so that said first telescoping tube is fully retracted into said second telescoping tube;

(f) continuing to withdraw said first catheter member so that said second telescoping tube is fully retracted into said third telescoping tube; and (g) gripping said proximal end of said second tubular catheter member and removing said telescoping catheter from said patient's vasculature.

26. A method for using a telescoping catheter, said telescoping catheter having a first elongated catheter member having a proximal end and a distal end, and a second tubular catheter member having a proximal end and a distal end and an inner diameter sized so that said first catheter member is slidably received within said second tubular catheter member, said second tubular catheter member comprising a first telescoping tube having distal and proximal ends, and a second telescoping tube having distal and proximal ends, said second telescoping tube having an inner diameter sized to permit said first telescoping tube to be retracted into said second telescoping tube, and said first elongated catheter member extending from said distal end of said first telescoping tube to beyond said proximal end of said second telescoping tube, said distal end of said first elongated catheter member engageable with said distal end of said first telescoping tube so that withdrawal of said first elongated catheter member through said proximal end of said second tubular catheter member will cause said first telescoping tube to be retracted into said second telescoping tube, said method comprising the steps of:

(a) inserting said telescoping catheter into a patient's vasculature;

(b) advancing said catheter to a predetermined location within said patient's vasculature while maneuvering said first and second telescoping tubes to a substantially fully extended position such that said proximal end of said first telescoping tube is located at about said distal end of said second telescoping tube;

(c) gripping said proximal end of said first catheter member and withdrawing said first catheter member through said second tubular catheter member;

(d) continuing to withdraw said first catheter member so that said first telescoping tube is fully retracted into said second telescoping tube; and (e) gripping said proximal end of said second tubular catheter member and removing said telescoping catheter from said patient's vasculature.

27. A method for using a telescoping catheter, said telescoping catheter having a first elongated catheter member having a proximal end and a distal end, and a second tubular catheter member having a proximal end and a distal end and an inner diameter sized so that said first catheter member is slidably received within said second tubular catheter member, said second tubular catheter member comprising a first telescoping tube having distal and proximal ends, a second telescoping tube having distal and proximal ends and a third telescoping tube having distal and proximal ends, said second telescoping tube having an inner diameter sized to permit said first telescoping tube to be retracted into said second telescoping tube, said third telescoping tube having an inner diameter sized to permit said second telescoping tube to be retracted into said third telescoping tube, and said first elongated catheter member extending from said distal end of said first telescoping tube to beyond said proximal end of said third telescoping tube, said distal end of said first elongated catheter member engageable with said distal end of said first telescoping tube and said first telescoping tube engageable with said second telescoping tube so that withdrawal of said first elongated catheter member through the proximal end of said second tubular catheter member will cause said first telescoping tube to be retracted into said second telescoping tube and said second telescoping tube to be retracted into said third telescoping tube, said method comprising the steps of:

(a) inserting said telescoping catheter into a patient's vasculature;

(b) advancing said telescoping catheter to a predetermined location within said patient's vasculature while maneuvering said first, second and third telescoping tubes to a substantially fully extended position such that proximal end of said first telescoping tube is located at about said distal end of said second telescoping tube and the proximal end of said second telescoping tube is located at about the distal end of said third telescoping tube;

(c) gripping the proximal end of said first catheter member and withdrawing said first catheter member through said second tubular catheter member;

(d) continuing to withdraw said first catheter member so that said first telescoping tube is fully retracted into said second telescoping tube;

(e) continuing to withdraw said first catheter member so that said second telescoping tube is fully retracted into said third telescoping tube; and (f) gripping said proximal end of said second tubular catheter member and removing said telescoping catheter from said patient's vasculature.

* * * * *